United States Patent [19]

Ruud

[11] Patent Number: 5,148,458
[45] Date of Patent: Sep. 15, 1992

[54] METHOD AND APPARATUS FOR SIMULTANEOUS PHASE COMPOSITION AND RESIDUAL STRESS MEASUREMENT BY X-RAY DIFFRACTION

[76] Inventor: Clayton Ruud, 331 First Ave., P.O. Box 459, Lemont, Pa. 16851-0459

[21] Appl. No.: 702,123

[22] Filed: May 16, 1991

Related U.S. Application Data

[63] Continuation of Ser. No. 467,007, Jan. 18, 1990, abandoned.

[51] Int. Cl.⁵ .............................................. G01N 23/20
[52] U.S. Cl. .................... 378/72; 378/71/70
[58] Field of Search ................ 378/72, 71, 73, 70, 378/82, 86, 90

[56] References Cited

U.S. PATENT DOCUMENTS

| | | | |
|---|---|---|---|
| 3,402,291 | 9/1968 | Weinman | 378/73 |
| 3,427,451 | 2/1969 | Spielberg | 378/73 |
| 3,868,506 | 2/1975 | Ogiso | 378/72 |
| 3,934,138 | 1/1976 | Bens | 378/72 |

Primary Examiner—Janice A. Howell
Assistant Examiner—Don Wong
Attorney, Agent, or Firm—Thomas J. Greer, Jr.

[57] ABSTRACT

It is often important to measure the phase composition and residual stress resultant from many materials processing procedures. For example, the carburization and heat treatment of steel components where the phase content of austenite versus ferrite or martensite, and residual stress are important characteristics with respect to the ultimate performance of the component. The x-ray diffraction techniques are used extensively to measure both of these characteristics of steel parts. However, the procedures for these measurements are time consuming and must be performed sequentially with any x-ray instrument except that of the present invention. This invention describes a method and apparatus that is able to perform the measurement of retained austenite and residual stress simultaneously. The advantages that the invention offers include very short measurement times and measurement of the characteristics in exactly the same spot of a sample at the same time.

5 Claims, 4 Drawing Sheets

METHOD AND APPARATUS FOR SIMULTANEOUS PHASE COMPOSITION AND RESIDUAL STRESS MEASUREMENT BY X-RAY DIFFRACTION

This is a continuation of application Ser. No. 07/467,007, filed Jan. 18, 1990 now abandoned.

BACKGROUND OF INVENTION

The application of x-ray diffraction (XRD) to the measurement of residual stress and/or elastic strain is a known technique. The application of XRD to the measurement of phase composition (retained austenite) is more widespread than that of stress and strain measurement and has been described in the literature. Laboratory instrumentation capable of sequentially measuring both of these characteristics have been developed. However, until now no laboratory or portable XRD instrument was capable of measuring both characteristics simultaneously. The remainder of this background section will focus upon residual stress and phase composition (retained austenite) measurement in steels.

RESIDUAL STRESS/ELASTIC STRAIN MEASUREMENT

The x-ray diffraction method is the only time-proven, truly nondestructive method for the measurement of residual stresses (elastic strain) in polycrystalline materials. Proof of its reliability lies in documentation of its use by thousands of engineers and scientists over the past four decades. These applications have spanned from stress analysis of uranium/zirconium fuel rods to aluminum alloy landing-gear components, and have included measurement of stresses in metal-powder-doped polymeric materials and tempering evaluation of carburized steels. The Society of Automotive Engineers considers the method of sufficient practical importance to have printed a Handbook Supplement on the subject three times.

Until recently, this non-destructive technology has been largely restricted to the laboratory due to peculiarities in the components involved and the design and construction of available equipment. Instrumentation for bringing this technology into the manufacturing area has advanced rapidly in the last few years toward increasing portability, compactness, and speed of operation of the equipment without serious reduction in its accuracy. Despite the marked improvements that have been made in this direction, there have been many demands for equipment that is still more portable, compact, and rapid than any of the devices available in the late 1970's or early 1980's. A paper by C. O. Ruud, P. S. Dimascio, and D. J. Snoha, "A Miniature Instrument for Residual Stress Measurement", Adv. in X-ray Anal., Vol. 27, Plenum Press, N.Y., 1984 and U.S. Pat. No. 4,686,631 describe the most portable type of instrument developed to date. This device incorporates a position sensitive scintillation detector (PSSD) described by C. O. Ruud, "Position-Sensitive Detector Improves X-Ray Powder Diffraction", I.R. and D., Jan. 1988, Pp. 84-87, which has been applied to tens of thousands of measurements using a prototype instrument as well as commercial versions of the instrument in industrial plants and government facilities.

When a metal or ceramic polycrystalline material is placed under stress, the elastic strain in the material is manifest in the crystal lattice of the individual grains. The stress applied externally or residual within the material, when below its yield strength, is taken up by interatomic strain. The x-ray diffraction method is capable of actually measuring the interatomic spacings, which are indicative of the macrostrain undergone by the specimen. Stress values are obtained from these elastic strains in the crystals by knowing the elastic constants of the material.

The important parameters involved in the mechanics of x-ray diffraction are described by the Bragg relation, $$\lambda n = 2d \sin \theta$$

where, $n = 1, 2, \ldots$ i.e., any integer; it is the order of reflection, and for stress work is usually unity
$\lambda$ = wave length of the diffracted radiation
$d$ = spacing of the reflected planes of atoms
$\theta$ = Bragg angle In all applications where the determination of d is required, either 1 or q is known. In most practical applications, including stress analysis, 1 is a constant and is known, and 2 q is measured. In a metal or ceramic powder where, particles show no preferred orientation, an x-ray beam only a few square millimeters in cross section is diffracted as a cone of x-ray beams by a large number of the randomly oriented crystallites (see FIG. 1). The cone's semi-apex angle $(180° - 2\theta)$ is not infinitely sharp, in that a plane perpendicular to the cone's axis would show the diffracted energy is distributed over a few tenths to several degrees of $2\theta$ (see FIG. 2). Therefore, the angular distribution of the diffracted beam intensity must be ascertained as a function of $2\theta$. In other words, the diffracted x-ray intensity must be measured at several angular positions or a continuum of positions, in order to determine the mean diffraction angle $2\theta$.

The basic equation relating x-ray diffraction principles to stress-strain relations can be written as $$\epsilon_{\phi\psi} = \frac{1 + \nu}{E} \sigma_\phi \sin^2 \psi - \frac{\nu}{E} (\sigma_1 + \sigma_2) \quad (1)$$

where, $\nu$ and E = elastic constants $\sigma_\phi$ = stress in the plane of the surface of the specimen at an angle of $\phi$ with a principal stress direction in the specimen surface $\Psi$ = angle between the surface normal and the normal to the crystallographic planes from which an x-ray peak is diffracted $\epsilon_{\phi\Psi}$ = strain in the direction defined by the angles f and y $\sigma_1$ and $\sigma_2$ = principal stresses in the surface plane of the specimen This may be rewritten as $$\sigma_\phi = \frac{d_{\phi\psi} - d_1}{d_1} \left( \frac{E}{1 + \nu} \right) \frac{1}{\sin^2 \psi} \quad (2)$$

where, $d_{\phi\Psi}$ = interatomic planar spacing for those crystal planes for which the normal is defined by the angles $\phi$ and $\Psi$, when $\Psi \neq 0$ $d_1$ = interatomic planar spacing for crystal planes parallel to the specimen surface, i.e., $\Psi = 0$ It should be noted that only those planes within a selected d-space range will be measured due to the narrow selection of Bragg angle imposed by the stress measurement arrangement. These planes are always of a specific Miller indice, i.e., (h k l), designation.

Now since the differences between $d_{\phi\psi}$ and $d_1$ is small, then from Bragg's Law $$\Delta d/d = -\cot\theta \left(\frac{\Delta 2\theta}{2}\right)$$

and Equation (2) may be rewritten as $$\sigma_\phi = (2\theta_1 - 2\theta\psi)\frac{\cot\theta_1}{2}\left(\frac{E}{1+v}\right)\frac{1}{\sin_2\psi}\left(\frac{\pi}{180}\right) \quad (3)$$

A variation of Equation (3) may be derived where $\Psi_1$ for $d_1$ is not zero degrees, this is called the single exposure technique (SET)[3].

PHASE COMPOSITION

The determination of phase composition of multiphase crystalline materials by XRD is used extensively in industry and academia. There are many examples of these analyses including the determination of rutile and anatase for paint pigments and retained austenite in steel components. We will focus upon the latter in the remainder of this specification but this invention could be applied equally well to a number of other phase analysis problems. An analytical problem of considerable complexity is the determination of retained austenite in steel. Austenite is an interstitial solid solution of carbon in g-iron (f.c.c.). Below 723° C. it normally decomposes into ferrite, a solid solution of carbon in a-iron (f.c.c.), and cementite ($Fe_3C$). During quenching or extremely rapid cooling, these two products may not have time to form, with the result that there is an unstable body-centered tetragonal product, martensite, usually with residual untransformed austenite. Because of the significant effects of this retained austenite on the properties of the steel, it is important to be able to measure quantitatively the amount present. Although dilatometric and magnetic measurements have been used for quantitative determination of austenite, they are volume properties and do not permit explorations of variation from point to point in a specimen. Quantitative x-ray diffraction, however, seems to be the perfect technique for this determination, except for the problem of calibrating the method.

The direct comparison method of XRD retained austenite measurement is of greatest metallurgical interest because it can be applied directly to polycrystalline aggregates. Since its development by Averbach and Cohen, it has been widely used for measuring the amount of retained austenite in hardened steel and will be described here in terms of that specific problem, although the method itself is quite general.

The hardening of steel requires two operations: (1) heating to a high temperature to form a homogeneous, face-centered-cubic solid solution called austenite, and (2) quenching the austenite to room temperature to transform it to a hard, metastable, body-centered-tetragonal solid solution called martensite. In practice, the quenched steel may contain some undissolved carbides and, because of incomplete transformation, some austenite on the service behavior of the steel is usually detrimental, but sometimes beneficial. At any rate there is considerable interest in methods of determining the exact amount of austenite present. Quantitative microscopic examination is fairly satisfactory as long as the austenite content is fairly high, but becomes unreliable below about 15 percent austenite in many steels. The x-ray method, on the other hand, is quite accurate in this low-austenite range, often the range of greatest practical interest.

Assume that a hardened steel contains only two phases, martensite and austenite. The problem is to determine the composition of the mixture, when the two phases have the same composition but different crystal structure. The external standard method is usually used, because the National Bureau of Standards (NBS) provides reference samples of known austenite content. In the basic intensity equation, $$K_2 = \left(\frac{I_o A\lambda^3}{32\pi r}\right)\left[\left(\frac{\mu_o}{4\pi}\right)^2 \frac{e^4}{m^2}\right] \quad (4)$$

and $$R = \left(\frac{1}{v^2}\right)\left[|F|^2 p\left(\frac{1+\cos^2 2\theta}{\sin^2\theta\cos\theta}\right)\right](e^{-2M}). \quad (5)$$

The diffracted intensity is then given by $$I = \frac{K_2 R}{2\mu}. \quad (6)$$

where $K_2$ is a constant, independent of the kind and amount of the diffracting substance, and R is a constant which depends on $\theta$, (h k l), and the kind of substance. Designating austenite by the subscript $\gamma$ and martensite by the subscript $\alpha$, we can write Eq. (6) for a particular diffraction line of each phase:

$$I_\gamma = \frac{K_2 R_\gamma C_\gamma}{2\mu_m}, \quad (7)$$

$$I_\alpha = \frac{K_2 R_\alpha C_\alpha}{2\mu_m}. \quad (8)$$

where $\mu_m$=linear x-ray absorption coefficient of the steel alloy, $C_\gamma$=concentration of austenite, and $C_\alpha$=concentration of martensite. Division of these equations yields $$\frac{I_\gamma}{I_\alpha} = \frac{R_\gamma C_\gamma}{R_\alpha C_\alpha}. \quad (9)$$

The value of $c_\gamma/c_\alpha$ can therefore be obtained from a measurement of $I_\gamma/I_\alpha$ and a calculation or experimental determination of $R_\gamma$ and $R_\alpha$. (Note that the calculation of R values requires a knowledge of the crystal structures and lattice parameters of both phases). Once $c_\gamma/c_\alpha$ is found, the value of $c_\gamma$ can be obtained from the additional relationship:

$$C_\gamma + C_\alpha = 1. \quad (10)$$

Thus it is possible to make an absolute measurement of the austenite content of the steel by direct comparison of the integrated intensity of an austenite line with the integrated intensity of a martensite line even without the NBS reference samples.

If the steel contains a third phase, namely, $Fe_3C$ (cementite), we can determine the cementite concentration either by quantitative microscopic examination or by diffraction. If we measure $I_c$, the integrated intensity of a particular cementite line, and calculate $R_c$ (a constant for cementite), then we can set up an equation similar to Eq. (9) from which $C_\gamma/C_c$ can be obtained. The value of $C_\gamma$ is then found from the relation $$C_\gamma + C_\alpha + C_c = 1. \tag{11}$$

In 1971 the National Bureau of Standards (NBS) began issuing the standard reference materials which contain specific amounts of austenite and cementite (i.e., iron carbide). There is now a fairly broad range of these standards available and they are used to experimentally provide calibration for the integrated x-ray intensity ratio in equation (9) versus the ratio of austenite to martensite content. One or more NBS standards then can be used to determine the $R_\gamma/R_\alpha$ ratio in equation (9) without the necessity of tedious calculation of the R constants. Usually a linear least square fit to intensity and concentration ratios over a range of austenite concentration of NBS standards is performed and the slope of the fit represents the R ratio. Thus, with the XRD method the determination of retained austenite can be made by measuring the integrated intensity of a martensite and an austenite peak.

INSTRUMENTATION

X-ray peaks in the far back-reflection range, i.e., peaks with $2\theta$ angles near 180°, are much preferred for stress measurement because they show the greatest change in diffraction angle with a given amount of applied or residual stress. Equation 3 shows that the greater the $\theta_1$ angle $(90 > \theta > 0)$, the greater the differences $(2\theta_1 - 2\theta_2)$ for a given stress. Also, for retained austenite determination on large samples using portable, or demountable type residual stress measurement devices, for example, see U.S. Pat. Nos. 4,095,103; 4,561,062; 4,686,631, x-ray peaks in the far back-reflection range are more convenient to use and less sensitive to focal distance and incident beam angle errors.

The art offers three main methods for measuring intensity versus the angle $2\theta$. These are:
1. Scanning goniometer (diffractometer)
2. Film camera
3. Position-sensitive detectors One-dimensional position-sensitive detectors (PSD), where the line of the detector is oriented coincident or tangent to the scanning circle, are increasingly being used in x-ray residual stress and retained austenite applications to more rapidly record diffraction profiles with equivalent spatial sensitivity to the scanning goniometer method (see U.S. Pat. Nos. 4,095,103; 4,561,062, and 4,686,631). However, geometric considerations differ considerably from the traditional diffractometer and require special attention. The apparatus and methodology described in U.S. Pat. No. 4,686,631 has eliminated many of the error sources which required attention, for example the specimen to detector distance errors encountered in other instruments. However, there is a keen interest in industry to simultaneously measure both characteristics of steel, i.e., residual stress and retained austenite, simultaneously and both in exactly the same volume of a steel component.

SUMMARY OF THE INVENTION

According to the practive of this invention, both stress in a polycrystalline sample or specimen (such as a machine component of alloy steel) as well as phase composition (retained austenite) are simultaneously determined by three x-ray detectors. This is in distinction to prior art techniques/apparatus which require, for such simultaneous determinations, a first pair of x-ray detectors for stress determination and a second pair of x-ray detectors for phase composition determination. In addition to the advantage of one less x-ray detector for sensing the Bragg reflections, this device provides unpreceidented speed of measurement, consistent with accuracy and capable of application to in-process measurements, and assures that the stress and phase analysis are performed on the same volume of material.

DETAILED DESCRIPTION OF THE INVENTION

Residual stress and phase composition measurement in polycrystalline metals and ceramics requires that tens of thousands of randomly oriented crystallites, or grains, be irradiated. Irradiation of so many crystallites is necessary in order to assure that several are oriented such that their selected set of (hkl) interatomic crystalline planes will diffract incident x-rays toward the detector surface to give a sufficient number of individual diffracted beams to provide a sufficient statistical sampling over the detector surface area (see FIG. 3). This sufficient sampling provides a peak shape representation from the polycrystalline sample such that the position of the apex, and the area, of the peak is assured to be representative of the average diffraction angle for the polycrystalline planes in position to diffract.

Figure 1:
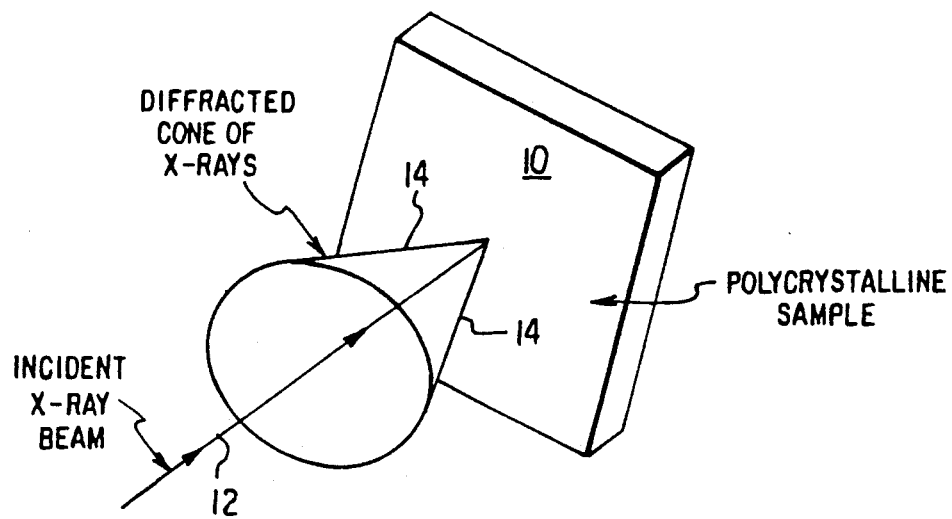
FIG. 1 shows a cone of radiation diffracted from an incident x-ray beam on a polycrystalline sample. The axis of the cone coincides with the transmitted beam.

In the application of conventional scanning detectors, the detector is moved through an arc perpendicular to the surface of the core shown in FIG. 1, for which the center of the arc is the irradiated area of the specimen and whose circumference is on a plane containing the cone axis. In the application of position sensitive detectors the line of the detector is oriented along the scanning direction previously described and as shown in FIG. 4.

Figure 4:
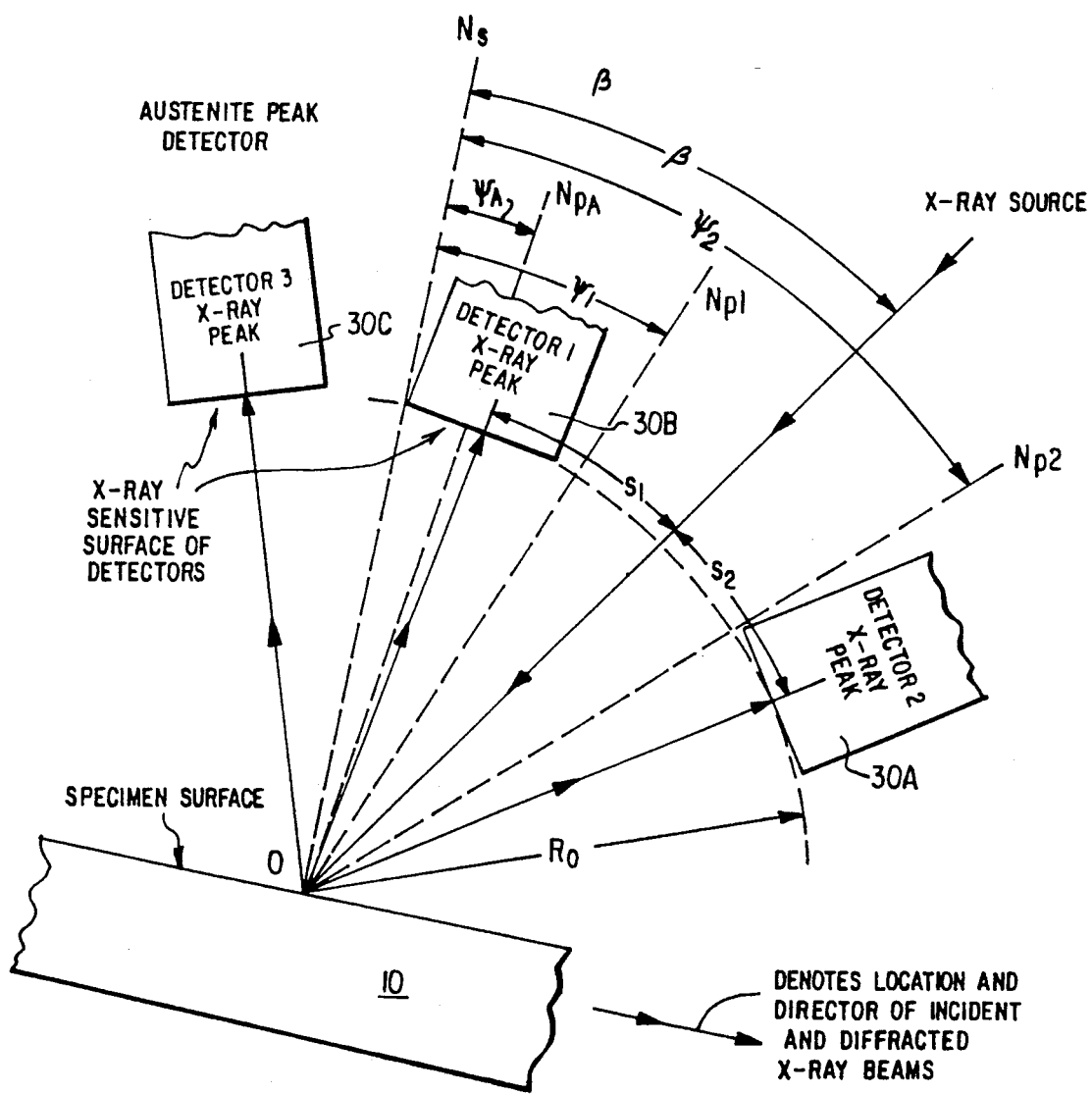
FIG. 4 is a schematic view of single-exposure technique (SET) of this invention showing the incident x-ray beam at an angle $\beta$ to the specimen surface normal (N) and two orientations of grains with sets of interatomic planes with normals $N_{p1}$ and $N_{p2}$ at angles of $\Psi_1$ and $\Psi_2$ to $N_s$. Also the third detector for retained austenite determination is shown at $\Psi_A$, which bisects the angle between the third detector and incident beam 12.

For residual stress measurement a plane stress condition is assumed to be extant in the material surface and diffracted peaks from two orientations of grains, usually designated with respect to psi ($\Psi$) angle (see FIG. 4), are measured to determine the angles, i.e., $\theta_1$ and $\theta_{105}$, from equation (3). These $\theta$ angles are often measured as a function of $S_1$ and $S_2$ for the following SET stress determination equation.

$$\sigma_\phi = \frac{E}{1+v} \frac{(S_2 - S_1)}{4 R_o \sin^2 \theta_o \sin^2 \beta}, \quad (12)$$

where $\theta_o$ is the Bragg angle of unstressed material, E and $v$ are elastic constants and the remaining quantities are defined in FIG. 4. There are two other commonly used XRD techniques for the determination residual stress and these are designated the double exposure technique (DET) and the multi-exposure technique. The former uses two beta ($\beta$) angles to obtain two psi ($\Psi$) angles where one psi angle is equal to zero and the latter uses multiple beta ($\beta$) angles per beta tilt and determines the stress from the slope of a linear least square fit to the data. There is also a variation of the positioning of x-ray detectors for residual stress measurement called the side-inclination method. This method makes use of an alternative positioning of position sensitive detector(s) or of scanning conventional detector(s) for the detection of the diffracted x-rays on the Debye ring so that the interatomic spacing d can be calculated. This method is used to apply either the double exposure or sin-square-psi techniques of stress measurement. The x-ray sensitive surface of the detector(s) are placed or scanned to intercept the diffracted cone of x-rays at a plane containing the incident x-ray beam, but perpendicular to the plane containing the b and h angles in FIG. 5, and this side incline plane intercepts the Debye ring at 90 gamma ($\gamma$) degrees from where the detectors are shown to intercept in FIG. 4.

Figure 5:
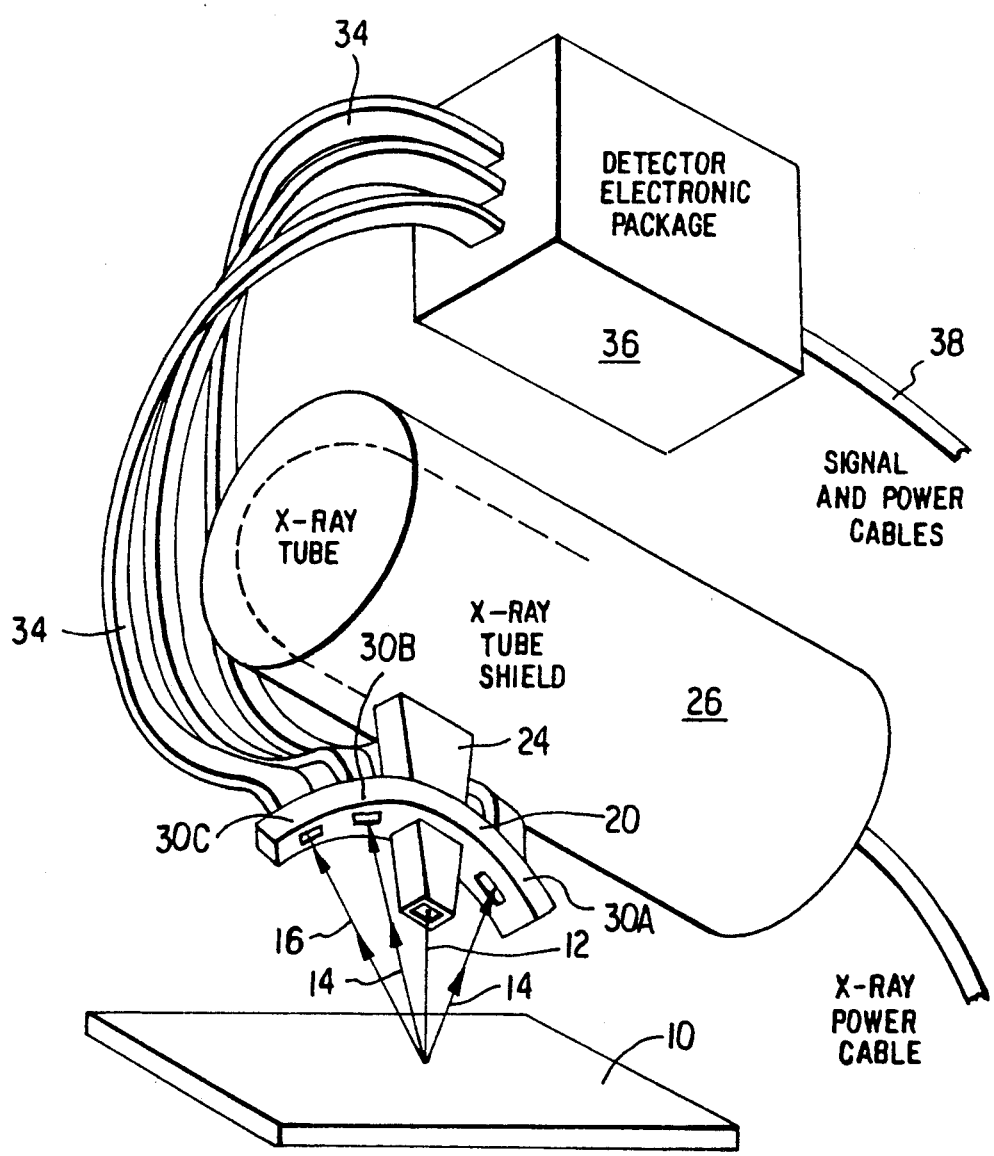
FIG. 5 is a partial perspective view of the elements shown in FIG. 4.

For phase composition analysis a third detector is shown in FIGS. 4 and 5, however additional detectors could be used in addition to a third detector to provide composition and/or stress information about other phases.

At FIG. 1, a polycrystalline sample 10, of steel for example, receives a beam 12 of incident x-radiation. The interaction of the x-rays on the atomic structure of the sample results in diffracted (Bragg reflection) rays 14 reflected back from the sample surface. Rays 14 define an imaginary cone whose circular base is termed a Debye ring.

Figure 2:
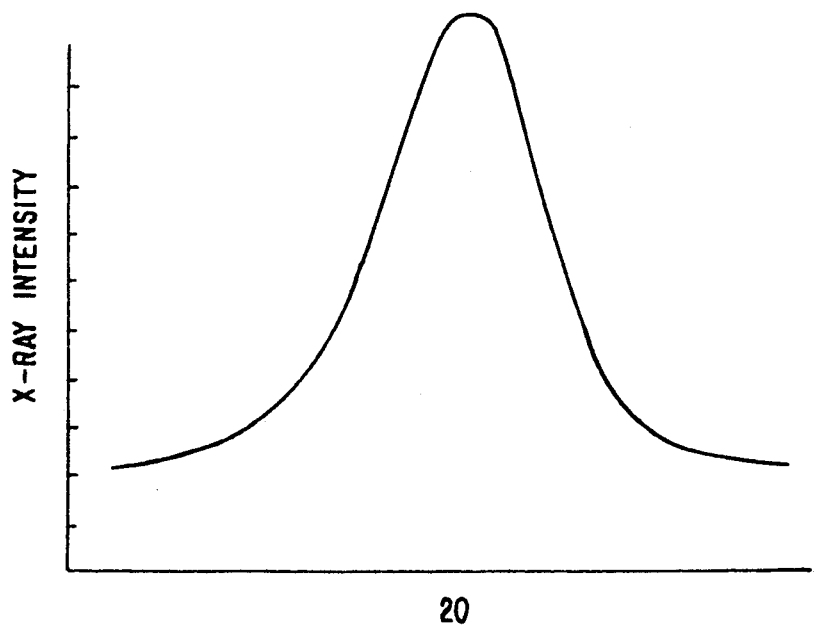
FIG. 2 is a plot of a typical diffracted x-ray intensity distribution against twice the Bragg angle in $2\theta$ degrees and it is the position of such a peak that is used to determine stress, and the area under it to determine phase composition.
Figure 3:
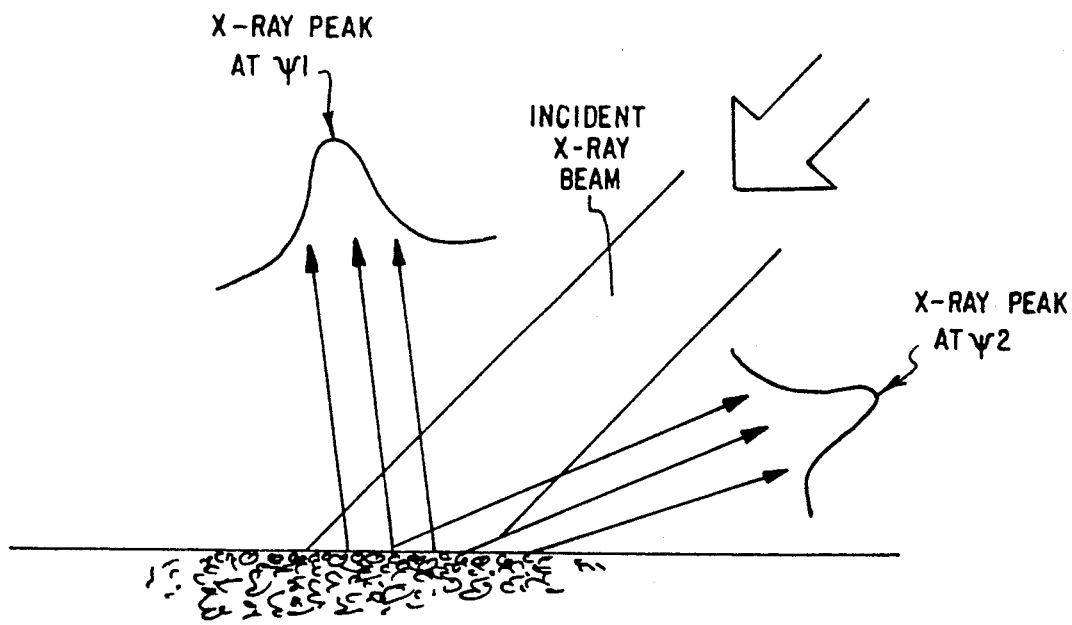
FIG. 3 is a schematic diagram showing the x-ray intensity distribution on two sides of the ring of the cone of x-rays shown in FIG. 1, i.e., the Debye ring, as diffracted from a polycrystalline sample at two psi ($\Psi$) angles, i.e. $\Psi_1$ and $\Psi_2$.

In FIG. 3 the plane of the figure is a plane in which the cone centroid lies, the centroid is also the incident x-ray beam, which is shown as a broad line instead of a single line as in FIG. 1. The plane of FIG. 3 intersects the cone shown in FIG. 1 at two places and the cone is depicted as three arrows in FIG. 3 indicating breadth to the diffracted beam. Further, the x-ray intensity across the cone is shown to vary in intensity as depicted by the peaks shown on either side of the broad cone in FIG. 3. These peaks are an x-ray intensity versus $2\theta$ distribution, as shown in FIG. 2.

In FIGS. 4 and 5 an apparatus is shown which includes several degrees of circular arc 20 mounted on a tube 24, the latter surrounding a beam of x-rays produced by an x-ray tube 25. Three x-ray detectors 30 are arranged on rigid, curved arm support 20, such that the detectors lie on an arc having a center approximately at the surface of sample 10. Each detector has a respective detector surface 30 A, 30 B, and 30 C. Cables 34 feed the output from each detector to detector storage and analysis means 36 such as shown in U.S. Pat. No. 4,686,631.

A typical procedure for simultaneous x-ray diffraction stress and analysis measurement on a high strength steel toothed gear or other sample involves the following steps.

Step 1: The stress and phase composition analysis apparatus shown in FIGS. 4 and 5 is positioned with respect to a gear sample (located at point 0 of FIG. 4) such that the incident x-ray beam emitting from the collimator strikes the specimen at a specimen surface normal to the incident beam angle ($\beta$ in FIG. 4) of about 24 degrees, and the distance between the specimen and x-ray detector surfaces (30A, 30B, and 30C in FIG. 5) is approximately 1.57 inches (40 mm).

Step 2: The x-ray detector(s) and x-ray source are then activated and a diffracted x-ray intensity distribution spectra such as shown in FIG. 3 for stress only is collected at 30A and 30B and a similar distribution is collected at 30C.

Step 3: The distribution spectra from the detector surfaces 30A, 30B, and 30C are then digitized and sent to a dedicated computer where they are stored and analyzed, for example the apparatus described in U.S. Pat. No. 4,686,631. The position of the peaks from 30A and 30B are determined, and from this analysis stress is calulated using the SET, or if more than one beta (b) angle is used using the DET or sin-square-psi technique. The intensity of one or both of the detector surface 30A or 30B peaks is then determined and compared with that from 30C for phase analysis, i.e., retained austenite determination.

What is claimed is:

1. An apparatus for enabling the simultaneous measurement of residual stresses in one or more crystalline phases as well as measuring the crystalline phase composition of an irradiated area of a material using x-ray diffraction, including first, second, and third position-sensitive x-ray detectors fixedly mounted along a circular arc, an x-ray source for directing an incident beam of x-rays towards the center of said circular arc, means for analyzing the distribution spectra detected by each of these detectors of the diffracted x-rays from a polycrystalline sample at the center of said arc.

2. A method of simultaneous measurement of residual stresses and the relative concentration of two or more solid crystalline phases including the steps of: directing a beam of x-rays on a polycrystalline sample to be analyzed, receiving and detecting resultant Bragg diffraction by three stationary position-sensitive x-ray detectors fixedly located along a circular arc at whose center said sample is located, analyzing the x-rays received by a pair of said detectors to determine residual stress and analyzing x-rays received by the third detector to determine phase composition of said sample.

3. The method of claim 2 wherein the stress is determined by the single exposure technique.

4. The method of claim 2 wherein the phase composition is determined by the external standard method.

5. The method of claim 2 wherein the stress is determined by the single exposure technique and wherein the phase composition is determined by the external standard method.

* * * * *